United States Patent [19]
Jose et al.

[11] Patent Number: 5,131,854
[45] Date of Patent: Jul. 21, 1992

[54] ELECTRICAL CONNECTOR FOR ATTACHING AN ELECTRODE TO A PATIENT IN A MEDICAL PROCEDURE

[76] Inventors: Rick Jose; Jeanne C. Jose, both of 224 Old Brattleboro Rd., Hindsdale, N.H. 03451

[21] Appl. No.: 707,849
[22] Filed: May 30, 1991
[51] Int. Cl.⁵ .................................................. H01R 4/58
[52] U.S. Cl. ...................................... 439/86; 128/640; 439/909
[58] Field of Search ................ 439/86, 886, 909, 931; 128/639–641

[56] References Cited

U.S. PATENT DOCUMENTS

| | | | |
|---|---|---|---|
| 4,016,869 | 4/1977 | Reichenberger | 128/2.1 E |
| 4,126,126 | 11/1978 | Bare et al. | 128/2.06 E |
| 4,239,046 | 12/1980 | Ong | 439/909 |
| 4,319,579 | 3/1982 | Cartmell | 128/640 |
| 4,632,121 | 12/1986 | Johnson et al. | 128/639 |
| 4,685,467 | 8/1987 | Cartmell et al. | 128/640 |
| 4,797,125 | 1/1989 | Malana | 439/729 |
| 4,938,219 | 7/1990 | Ishii et al. | 128/640 |

Primary Examiner—Paula A. Bradley
Attorney, Agent, or Firm—Terry M. Gernstein

[57] ABSTRACT

A connector includes a Y-shaped one-piece body formed of plastic material that has been coated with an electrically conductive substance. The body has a yoke-like head having a sloping entrance slot formed thereon whereby prong-shaped electrodes can be inserted into the connector in a variety of manners. The connector can be used in a variety of medical procedures.

5 Claims, 3 Drawing Sheets

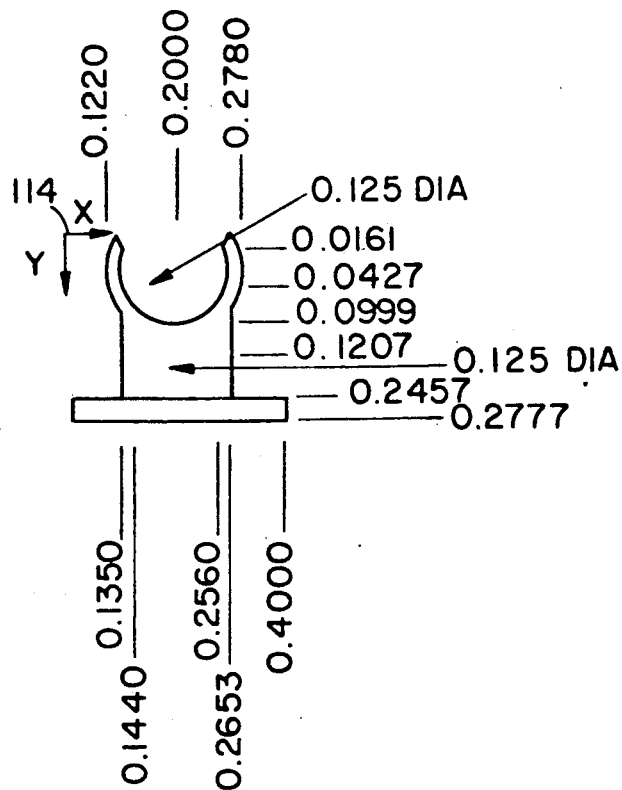
FIG. 3A
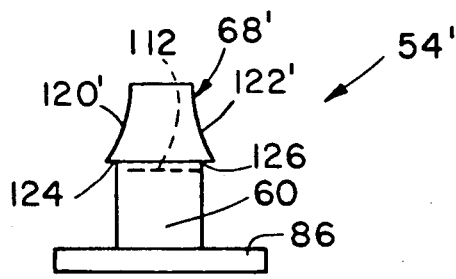
FIG. 6
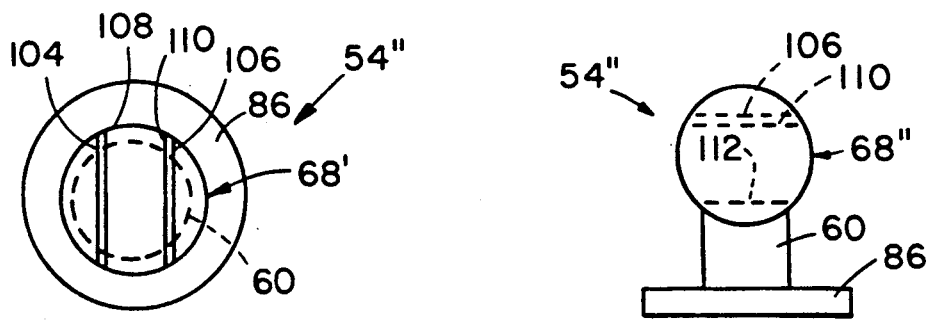
FIG. 7
FIG. 8

ELECTRICAL CONNECTOR FOR ATTACHING AN ELECTRODE TO A PATIENT IN A MEDICAL PROCEDURE

TECHNICAL FIELD OF THE INVENTION

The present invention relates to the general art of electrical connectors, and to the particular field of electrical connectors used in medical procedures.

Background of the Invention

Electrodes through which electrical current or electrical signals pass are often used in medical procedures, such as EKGs, electrical stimulus procedures, or the like. These electrodes are generally releasably attached to a patient by various connector means that, themselves, are releasably mounted on a patient. In such a set up, a mounting element, such as an adhesive covered pad, is releasably fixed to the patient and that pad holds an electrical connector in electrical contact with the patient. An electrode is releasably attached to the connector and to a monitoring system.

While this electrical connection system has worked well in the past, recent developments in the medical field have created problems for such systems. For example, as more procedures are carried out on a single patient, the process of connecting and disconnecting the electrode to and from the connector becomes important. A technician would like the option of making a connection in a variety of ways. Furthermore, many present connectors, such as alligator clips, are susceptible to forming loose connections with the electrode. This problem may become more important as the connector ages. Still other connectors are susceptible to causing interference with the signal or electrical impulse being sent to or from the patient, especially if the connector has deteriorated.

Still further, due to the existence of various communicable diseases, such as AIDS and HIV viruses, many prior art electrodes are being held in disfavor because they may tend to transmit such viruses or contaminate connectors and electrodes. Therefore, some health care providers are using disposable electrodes. Many of these disposable electrodes have heads that are prong-like in shape, and many prior art connectors are not amenable for use with such new disposable electrodes. It can become quite costly for a health care provider to adapt electrodes and/or connectors to accommodate such disposable electrodes.

Therefore, there is a need for an electrical connector for use in medical procedures which connector is amenable to several modes of connection to any electrode, especially a disposable electrode, and which will not interfere with the electrical signal traversing the connector and will not deteriorate over time.

Objects of the Invention

It is a main object of the present invention is to provide an electrical connector for use in medical procedures.

It is another object of the present invention to provide an electrical connector for use in medical procedures and which is amenable for use in conjunction with disposable electrodes.

It is another object of the present invention to provide an electrical connector for use in medical procedures and which is amenable for use in conjunction with prong-like electrodes.

It is another object of the present invention to provide an electrical connector for use in medical procedures that will not interfere with the signal or current being sent to or received from a patient.

It is another object of the present invention to provide an electrical connector for use in medical procedures and which is amenable for use in a variety of manners.

It is another object of the present invention to provide an electrical connector for use in medical procedures and which can be used in a variety of manners without endangering that connector.

Summary of the Invention

These, and other, objects are achieved by a one-piece electrical connector having a Y-shaped body mounted on a base that can be embedded in an adhesive-covered mounting pad. The Y-shaped body has a neck section on which a yoke-like head is mounted. The neck section is cylindrical and has a diameter measured between two side surfaces. The yoke-like head has an opening on top thereof and is connected to the neck on the bottom thereof. In one form of the invention, the head has two faces each of which is in a plane that also contains a corresponding outer surface of the neck. In a second form of the invention, the head has two planar faces that are each offset from the planes containing corresponding neck faces.

The yoke-like head also includes a tapered entrance slot through which the electrode passes. The slot is tapered in a manner that permits the electrode to easily enter the slot, yet will be securely held in the head. The tapered nature of the slot also permits the connector to be used a plurality of times without loss or degradation of its electrode grasping capability.

In this manner, a prong-like head of an electrode can be slipped into the yoke-like connector head either via the tapered slot on top of the connector head, or slipped into the connector head along the longitudinal axis of the prong-like electrode. This will permit a technician to attach the electrode to the connector in a variety of ways, including snapping the electrode into the connector or slipping it into the connector thereby providing versatility to the system without endangering the connector.

Still further, the Y-shaped connector of the present invention is amenable to use with disposable electrodes. This permits the connector to be used in a manner that will not contaminate various parts of the system. Another form of the connector includes a spherical head that is sized and shaped identically to the spherical head of present snap-in connectors. This form of the connector will thus be amenable to use in conjunction with presently available snap-on electrodes in addition to use in the above-mentioned manners.

Since the connector is one piece in construction, it is quite strong and is not susceptible to interfering with an electrical signal or current passing to or from the electrode. The one-piece nature of the connector also contributes to a long life for the electrode.

The connector can be used in all type of medical procedures, including, but not limited to, EKG monitoring, electrical stimulation and the like.

Brief Description of the Drawing Figures

FIG. 3A is a front elevational view thereof showing a coordinate axis and the various dimensions associated therewith.

FIG. 6 is a side elevational view of an alternative form of the electrical connector of the present invention.

FIG. 7 is a top plan view of an alternative form of the connector in which the head thereof is spherical.

FIG. 8 is a side elevational view of the FIG. 7 embodiment, it being noted that the front and rear elevational views thereof will be identical to FIG. 3.

Detailed Description of the Preferred Embodiment of the Invention

Figure 1:
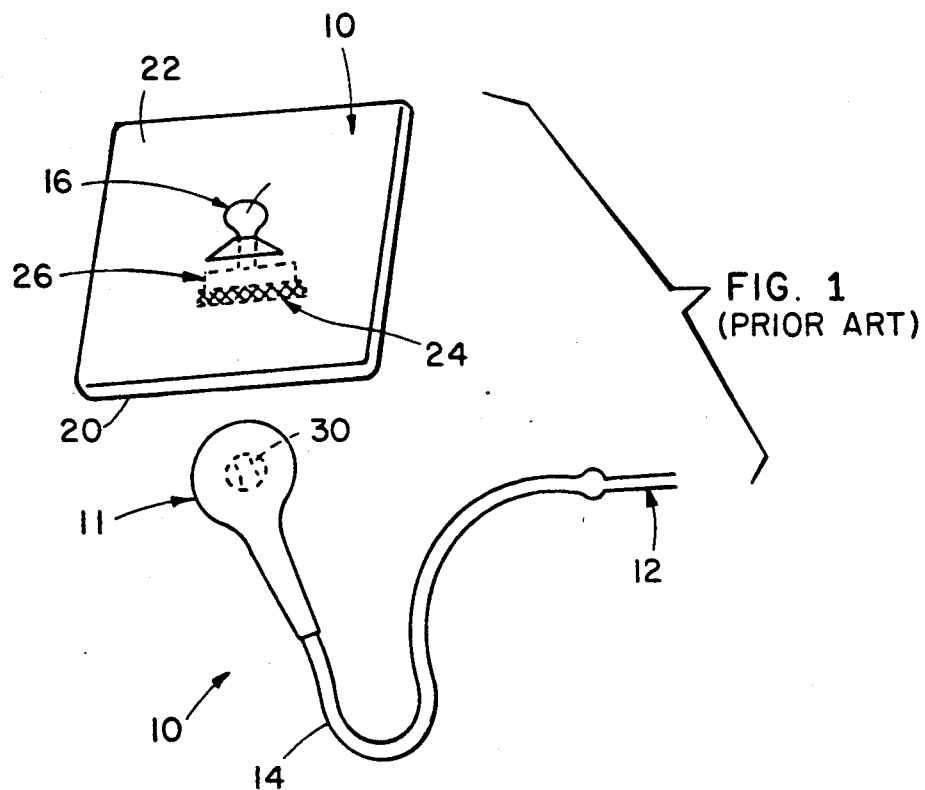
FIG. 1 is a perspective view of a prior art electrical connector and electrode.

Shown in FIG. 1 is a prior art electrode 10, having a head 11 that is connected to a monitoring system (not shown) via a prong-like electrode 12, mounted on a line conductor 14. The electrode 12 is releasably attached to a ball-shaped connector 16 that is mounted on a patient by means of a mounting pad 18. The pad 18 has a backing surface 20 that is covered with adhesive used to releasably mount that pad on a patient, and a top surface 22. The pad can be formed of polyethylene foam material or the like, and the connector 16 is mounted in a bed of potassium chloride-soaked foam 24.

The connector 16 includes a base 26 and a spherical head 28 that snaps into and out of a concave spherical opening 30 defined in the electrode 10 to electrically connect the electrode to the patient via the connector 16. The base 26 is a silver-silver chloride plated ABS material, and the connector is formed of steel.

Figure 2:
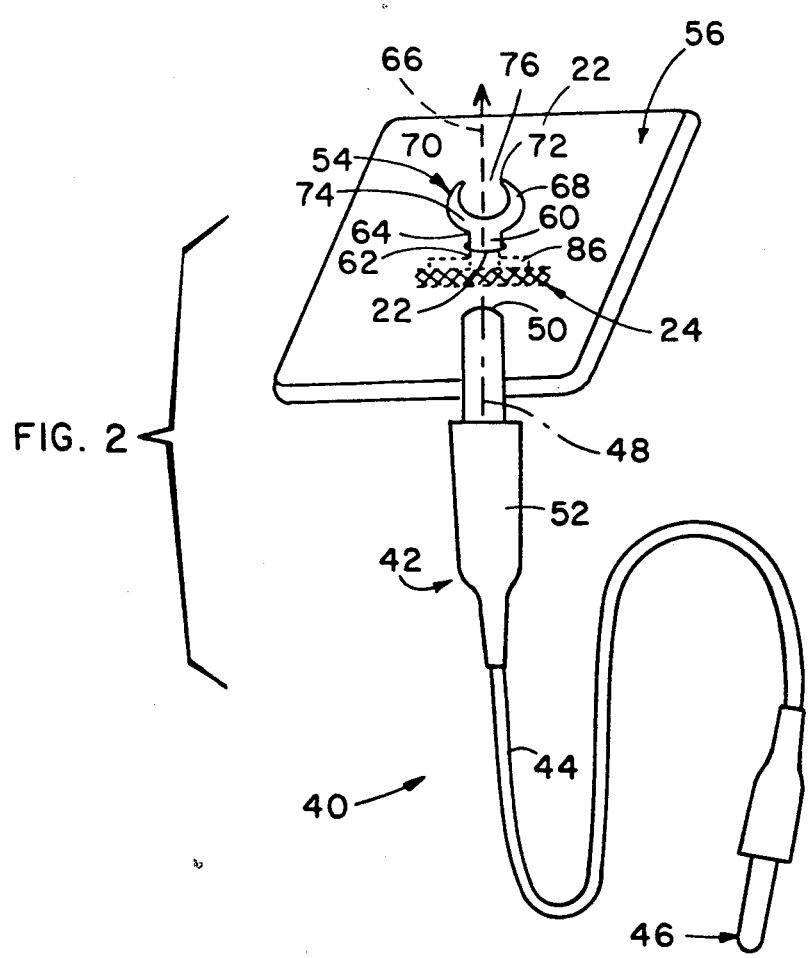
FIG. 2 is a perspective view of an electrical connector of the present invention in conjunction with a prong-like electrode.
Figure 5:
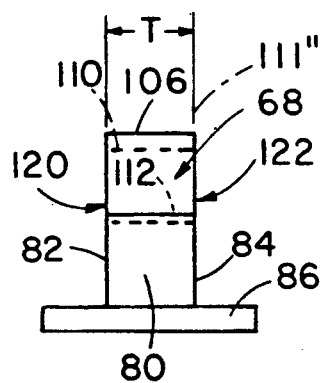
FIG. 5 is a side elevational view of the electrical connector of the present invention.
Figure 4:
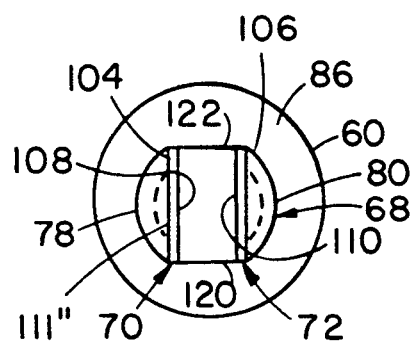
FIG. 4 is a top plan view of the electrical connector of the present invention.

An electrode 40 is shown in FIG. 2 as having a prong-like head 42 on one end of a line conductor 44 and a plug 46 on the other end of the line conductor. The prong-like head 42 has an axial centerline 48 extending from a leading tip 50 thereof toward a body 52.

An electrical connector 54 is shown in FIGS. 2-5 and is used in conjunction with the electrode 40. The connector 54 is one piece and is mounted on a mounting pad 56 that is identical to the mounting pad 18 discussed above to be releasably and electrically connected to a patient during a medical procedure.

The connector 54 is Y-shaped and includes a cylindrical neck portion 60 having a proximal end 62 adjacent to the top surface 22 of the mounting pad 56 and extending upwardly therefrom to a distal end 64. The neck portion also includes a longitudinal axis 66 extending between the proximal and distal ends thereof. A yoke-like head 68 is mounted on top of the neck portion and has two spaced apart ends 70 and 72 spaced from a bight portion 74 that is connected to the neck portion. The ends are spaced from the bight portion along the axis 66 and are spaced from each other by a gap 76 extending transverse to the axis 66. The gap 76 is actually a complex gap as will be discussed below. The connector 54 has the base thereof embedded in the pad 56 and has the neck thereof extending out of that pad. This configuration is indicated in FIG. 2 with pad top surface 22 being indicated adjacent to the neck portion.

The connector neck portion includes surfaces 78 and 80 that are diametrically spaced from each other transverse to the axis 66 and define a width dimension W for the neck portion. The neck portion is cylindrical and includes a first section 82 and a second section 84 that are diametrically spaced apart from each other transverse to the axis 66 and transverse to the spacing between surfaces 78 and 80 to define a thickness dimension T for the neck portion. A circular mounting base 86 is connected to the neck and is embedded in the mounting pad 56.

The width dimension W of the connector 54 can exceed the thickness dimension T or can be essentially equal to that dimension.

The yoke-like head 68 is located on top of the neck portion distal end, and has two outer side surfaces 100 and 102 that are located adjacent to the neck side surfaces 78 and 80 respectively and extend accurately outwardly from such neck side edges to points 104 and 106 respectively located coplanarly with the neck side surfaces 78 and 80, respectively. The head surfaces 100 and 102 slope downwardly and radially inwardly from the points 104 and 106 to inner edges 108 and 110 respectively. The points 104 and 106 are spaced apart from each other by a gap 111, and the inner edges 108 and 110 are spaced apart from each other by a second gap 111'. The first gap 111 is larger than the second gap 111' whereby an entrance slot is formed that slopes inwardly and downwardly with respect to the head 68. The entrance slot has a sloping surface 111" that slopes at a 30° angle with respect to the axis 66. The head 68 has an inner surface 112 connecting the inner edges 108 and 110 in a smooth and continuous manner.

The electrode head 42 can be inserted into the connector head by sliding that head 42 into the connector head along the axis 48 or by snapping the connector head down through the inwardly sloping entrance slot. The orientation of the edges 104 and 106 with respect to the edges 108 and 110 permits the electrode to easily move into the area 130 but will form an interference fit around that electrode once it is in the area 130 to prevent the electrode from moving out of the area 130 via the entrance slot without exerting considerable force on the yoke sides to force them apart far enough to permit the electrode to pass by the edges 108 and 110.

The dimensions of the connector are indicated in FIG. 3A with respect to an x-y coordinate axis that has been overlaid onto the connector in FIG. 3A. The coordinate axis has its origin at location 114, its positive y-axis extending from the origin towards the base 86, and its positive x-axis extending toward the head 68 from the origin. The positive axes are indicated in FIG. 3A by the arrows x and y, and the dimensions are shown in FIG. 3A on that coordinate axis. The preferred thickness T is in the range of 0/005" to 0.08"; however, other sizes can be used without departing from the scope of the present invention.

In the preferred form of the connector 54, the one-piece body is formed of plastic material that has been coated by an electrically conductive material, such as silver/silver chloride.

The head 68 has a first face 120 located to be coplanar with a plane containing the neck first surface 82 and a second face 122 located to be coplanar with a plane containing the neck second surface 84. The head also has a width dimension WH measured between the two surfaces 100 and 102 that exceeds neck width dimension W. Therefore, the head 68 has a thickness equal to dimension T of the neck, and a width dimension WH that exceeds the neck width dimension W. However, the head width dimension can exceed the head thickness dimension if suitable.

A second form of the connector is shown in FIG. 6 as connector 54'. The connector 54' has a neck 62 that is identical to the neck 62 of connector 54, and a head 68' mounted on top of that neck. The head 54' is similar to the head 68, and has a first surface 120' located adjacent to neck first surface 82 and a second surface 122' located adjacent to neck second surface 84. The face 120' is concave and is spaced from the plane containing the neck surface 82, and the face 122' is also arcuate and is spaced from the plane containing the neck second surface 84 whereby steps 124 and 126 are formed adjacent to the neck distal end.

Figure 3:
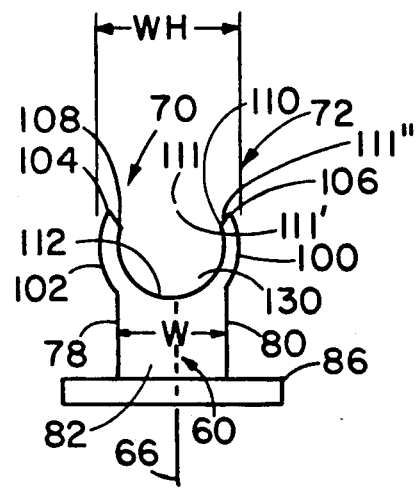
FIG. 3 is a front elevational view of the electrical connector of the present invention.

A third form of the connector is shown in FIGS. 7 and 8 as connector 54". The connector 54" includes a spherical head 68" that is sized and shaped to have an outer perimeter identical to the head 28 shown in FIG. 1. This configuration will permit the connector 54" to be used in conjunction with the electrode 10. However, the connector 54" also includes an inwardly sloped entrance slot as discussed above with an inner area 130 as discussed above. Therefore, the connector 54" can be used in the same manner as discussed above in regard to connectors 54 and 54', yet can also be used in conjunction with electrodes such as electrode 10. The connector 54" is shown only in top plan view and in side elevational view because its front and rear elevational views will be identical to the front and rear elevational views of the connector 54 as indicated in FIG. 3.

The connector of the present invention can accommodate electrodes having any size in the range of 0.040" to 0.187", and can be used in any substrate with any conductive medium such as liquid or solid conductive gels. It is noted that for medical procedures using electrical stimulation, the conductor is coated with silver only.

It is understood that while certain forms of the present invention have been illustrated and described herein, it is not to be limited to the specific forms or arrangements of parts described and shown.

We claim:

1. An electrical connector for attaching electrodes to a patient during a medical procedure comprising:
   a mounting pad having a to surface and a bottom surface;
   attaching means on said pad bottom surface for releasably attaching said pad to a patient during a medical procedure; and
   a one-piece connector fixedly mounting on said mounting pad and extending from said pad top surface, said connector including
   a base fixed to said mounting pad,
   a neck having a proximal end connected to said base, a distal, end spaced from said base, a first surface, a second surface, two side surfaces, a width dimension measured between said side edges, and a thickness dimension measured between said first and second surfaces, and a neck axis extending from said proximal end to said neck distal end, and
   a yoke-like head on said neck distal end, and including
   two side surfaces extending from said neck distal end upwardly from said distal end, said head side surfaces being arcuate and having a first point thereon,
   a second point on each head side surface adjacent to said first point of each head side surface and spaced from said first point toward said neck and inwardly toward the other head side surface,
   said first points being separated from each other by a first gap, and said second points being separated from each other by a second gap, said first gap being larger than said second gap,
   an entrance surface connecting each first edge to a second edge located adjacent thereto to define an entrance slot that slopes inwardly and downwardly with respect to said head,
   a first surface adjacent to said neck first surface,
   a second surface adjacent to said neck second surface, and
   an arcuate inner surface smoothly and continuously connecting said second points together.

2. The electrical connector defined in claim 1 wherein said entrance surface is angled at 30° with respect to said neck axis.

3. An electrical connector for attaching electrodes to a patient during a medical procedure comprising:
   a mounting pad having a top surface and a bottom surface;
   attaching means on said pad bottom surface fore releasably attaching said pad to a patient during a medical procedure; and
   a one-piece connector fixedly mounted on said mounting pad and extending from said pad top surface, said connector including
   a base fixed to said mounting pad,
   a neck having a proximal end connected to said base, a distal end spaced from said base, a first surface, a second surface, two side surfaces, a width dimension measured between said side surfaces, and a thickness dimension measured between said first and second surfaces, and a neck axis extending from said proximal end to said neck distal end, and
   a yoke-like head on said neck distal end, and including
   two side surfaces extending from said neck distal end upwardly from said distal end, said head side surfaces being arcuate and having a first point thereon,
   a second point on each head side surface adjacent to said first point of each head side surface and spaced from said first point toward said neck and inwardly toward the other head side surface,
   said first points being separated from each other by a first gap, and said second points being separated from each other by a second gap, said first gap being larger than said second gap,
   an entrance surface connecting each first edge to a second edge located adjacent thereto to define an entrance slot that slopes inwardly and downwardly width respect to said head, a first surface adjacent to said neck first surface and being spaced apart therefrom, a second surface adjacent to said neck second surface and being spaced apart therefrom, a first shoulder formed between said first surface and said first neck surface, a second shoulder formed between said second surface and said second neck surface, and an arcuate inner surface smoothly and continuously connecting said second points together.

4. The electrical connector defined in claim 3 wherein said one-piece body is formed of plastic material.

5. The electrical connector defined in claim 4 further including an electrically conductive coating on said one-piece body.

* * * * *